United States Patent
Palmer-Felgate

(10) Patent No.: US 8,657,780 B2
(45) Date of Patent: Feb. 25, 2014

(54) APPLICATION DEVICE

(75) Inventor: John Paul Palmer-Felgate, Horsham (GB)

(73) Assignee: Schott Schweiz AG, St. Gallen (CH)

( * ) Notice: Subject to any disclaimer, the term of this patent is extended or adjusted under 35 U.S.C. 154(b) by 1078 days.

(21) Appl. No.: 12/688,088

(22) Filed: Jan. 15, 2010

(65) Prior Publication Data
US 2010/0211016 A1 Aug. 19, 2010

Related U.S. Application Data

(63) Continuation of application No. PCT/EP2008/005867, filed on Jul. 17, 2008.

(30) Foreign Application Priority Data

Jul. 25, 2007 (EP) .................................. 07 014 576

(51) Int. Cl.
*A61M 37/00* (2006.01)

(52) U.S. Cl.
USPC .......................................................... 604/91

(58) Field of Classification Search
USPC .................................. 604/192, 91
See application file for complete search history.

(56) References Cited

U.S. PATENT DOCUMENTS

| 3,638,650 A | 2/1972 | Burke et al. |
| 4,720,285 A | 1/1988 | Pickhard |
| 2005/0177100 A1* | 8/2005 | Harper et al. .................... 604/89 |
| 2005/0215952 A1 | 9/2005 | Brunel et al. |

FOREIGN PATENT DOCUMENTS

| DE | 2145962 | * | 3/1973 |
| GB | 2 145 962 | | 3/1973 |
| WO | WO 86/03126 | | 6/1986 |
| WO | WO 96/13171 | | 5/1996 |
| WO | WO 2005/039669 A2 | | 5/2005 |

* cited by examiner

*Primary Examiner* — Kevin C Sirmons
*Assistant Examiner* — Deanna K Hall
(74) *Attorney, Agent, or Firm* — Harness, Dickey & Pierce, P.L.C.

(57) ABSTRACT

An application device for applying a dispensable material is disclosed having a closed state and an open state, the application device comprising an elastic part made of an elastic material and having a through channel being configured for engaging a cavity of a receptacle, further comprising a holder supporting a dispensing means fluidly connected with the through channel. A pinch seal is used for sealing the through channel when being in the closed state. Long-term storage is made possible, since leakage of the pinch seal is prevented by a cap effecting the pinch seal which is partially fitted into a collar.

14 Claims, 1 Drawing Sheet

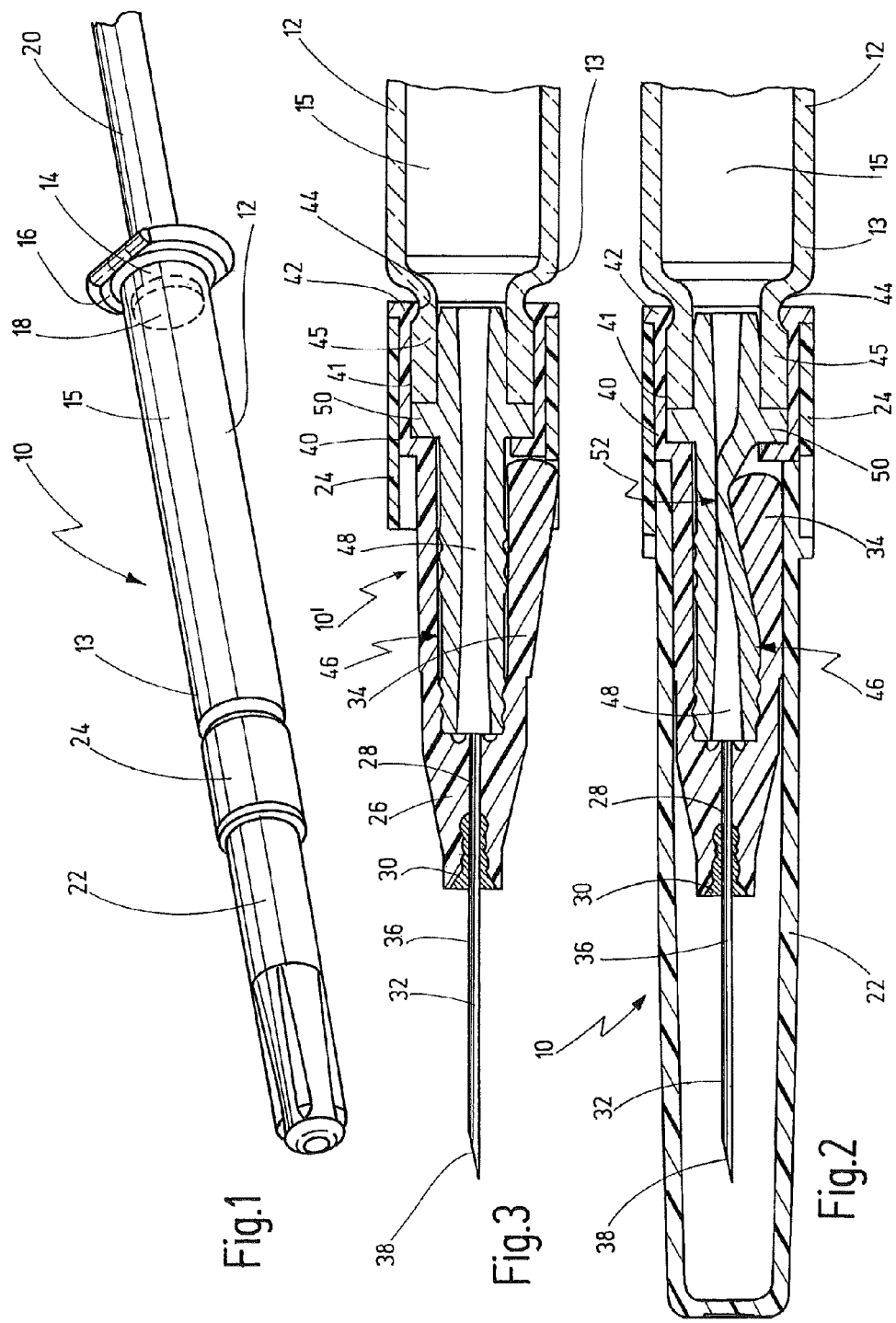

APPLICATION DEVICE

RELATED APPLICATIONS

This is a continuation application of copending International Patent Application PCT/EP2008/005867 which was filed on Jul. 17, 2008 and published in English, and claims priority of European Patent Application 07014576.8 filed on Jul. 25, 2007. The entire contents of these priority applications are fully incorporated herein by reference.

BACKGROUND OF THE INVENTION

The invention relates to an application device for applying a dispensable material that is stored in a cavity of some kind of a receptacle. More particularly, the material may be a liquid, semi-liquid, pasty or powdered material preferably used for medical, diagnostic, cosmetic or dental applications. The application device comprises a closed state and an open state. It may be configured as an injection device configured for single or multiple use and having a closed state and an open state.

From US 2005/0215952 A1 an application device configured as a single-use syringe is known which comprises:
  a tubular receptacle enclosing a cavity for receiving a liquid;
  a bung made of an elastic material being held at a first longitudinal end of the tubular receptacle and comprising a through channel that is fluidly connected with the cavity;
  a holder engaging the bung; and
  a needle secured within the holder and comprising a delivery duct fluidly connected with the through channel.

The known syringe includes a tubular receptacle provided with sealingly closing-off elements delimiting a chamber, intended to be filled with a liquid, and having a liquid-delivery duct opening into the chamber, a needle-carrying base having a duct for supplying a liquid to the needle and being axially movable between a retracted position in which the delivery duct is closed-off, and an advanced injection position in which it allows the liquid to flow out of the chamber to the needle, a cap having a shape adapted to cover the base and provided with elements for detachable connection to the tubular receptacle, axial-stop elements arranged so as to keep the base in its closing-off position when the latter is covered by the cap, and axial stop elements arranged so as to limit the axial displacement travel of the base, once the cap is removed.

The known device suffers from several draw-backs: First of all the opening and closing system of the syringe relies on clips made of hard plastic material that engage recesses provided on the holder. Reliability of the working of these clips is based on plastic molded parts and relative tolerances between these parts.

Also the basic principle of this syringe for moving from the closed state to the open state is based on a sliding seal. There is the potential risk of a blocking of the seal after extended storage time. If the axial movement is impeded or blocked in some way, then there is the risk that the syringe may not be activated to allow an injection of the stored liquid to a patient.

There is a variety of other so-called "dry needle" application devices, comprising a tubular receptacle containing the liquid to be injected and closed off by a membrane, and a double-point needle which can be displaced axially relative to the tubular receptacle so as to pierce the membrane at the moment of injection. (DE 2 055 840; U.S. Pat. No. 4,720,285; WO 96/013171).

The provision of a membrane seal poses a complication of the manufacturing process. In addition, there is always a necessary activation movement either by twisting of the cap or by an axial displacement of the part penetrating the membrane.

Again, there is the risk of blocking of the penetrating needle so that the syringe may not be activated. Further there is the risk of generating particles as well.

SUMMARY OF THE INVENTION

In view of this it is a first object of the invention to disclose an improved application device for applying a material stored within a cavity which is easy to manufacture and can be conveniently and reliably be activated for use.

It is a second object of the invention to disclose an improved application device for applying a material which is suitable for long-term storage the material stored within the application device.

It is a third object of the invention to disclose an improved application device which can be used as ready-to-use syringe filled with a medical material.

It is a forth object of the invention to disclose an improved application device that can be used as a ready-to-use syringe filled with a medical material that avoids leakage after long-term storage.

It is a fifth object of the invention to disclose an improved method for manufacturing an application device that is pre-filled with a material to be applied.

According to the invention these and other objects of the invention are achieved by an application device for applying a dispensable material, the application device having a closed state and an open state and comprising:
  an elastic part made of an elastic material and having a through channel being configured for engaging a cavity of a receptacle;
  a holder comprising a support for receiving a dispensing means fluidly connected with the through channel; and
  a pinch seal sealing the through channel when being in said closed state.

The object is fully achieved in this way.

Namely, the sealing is effected in a very simple way.

If possibly after extended storage time there should occur some sticking within the through channel so that the pinch seal is permanently blocked, it may be opened by exerting a pressure.

Alternatively, or in addition, the internal surface of the through channel of the elastic said elastic part may comprise a coating made of a material preventing sticking of the internal surface and interaction with any dispensable material filled into the cavity of the receptacle. This coating may, e.g. be a parylene or PTFE coating.

So there is no risk that the application device cannot be transferred into its open state even after extended storage life.

According to a preferred embodiment of the invention a cap is fitted onto a peripheral portion of the holder for compressing the holder at least partially to effect the pinch-seal. Further, the cap may comprise an end portion that at least partially fits into the collar, in particular into a hollow tubular portion of the collar.

These features help to facilitate a long-term sealing of a material obtained within the cavity of the receptacle. While the cap may consist of a material that may be subject to creeping during long-term storage, such possible creeping is prevented by the collar that may consist of a more stable material.

According to a further feature of the invention the elastic part comprises a peripheral flange resting against an end portion of the receptacle, the peripheral flange being sealed against said end portion by the holder which at least partially encloses the peripheral flange and secures it to the end portion of the receptacle.

Thus the application device includes an integrated sealing of the cavity of the receptacle with the delivery means or needle connected thereto.

According to a preferred embodiment of the invention the receptacle is configured as a syringe barrel, cartridge, vial, bottle or bag.

According to a further embodiment of the invention the dispensing means is configured as a needle or as a coupling, in particular as a Luer-Lock thread, for attaching a part.

So the dispensing means may preferably be coupled to a needle so as to allow an injection of the material stored within the cavity into a patient or into an animal, or to allow a direction into any other part attached by some sort of coupling such as a Luer-Lock thread, a bayonet type connector etc.

According to a further development of the invention the elastic part is configured as a bung at least partially received within the holder.

This allows for a simple design and easy activation or deactivation of the pinch seal.

According to a further embodiment of the invention the application device further comprises:
- a receptacle enclosing a cavity for receiving a dispensable material;
- a bung made of an elastic material being held at a first longitudinal end of the receptacle and comprising the through channel that is fluidly connected with the cavity;
- a holder engaging the bung; and
- a needle secured within the holder and comprising a delivery duct fluidly connected with the through channel.

In this way the application device is configured as a syringe.

According to a further development of the invention the application device further comprises:
- a removable cap supported on a peripheral portion of the holder when being in the closed state;
- wherein the cap, when being in the closed state, compresses the peripheral portion of the holder at least partially, thereby effecting the pinch seal; and
- wherein the pinch seal of the through channel is released, when the cap is removed, thereby allowing delivery of the dispensable material from the cavity through the through channel to the dispensing means, in particular through a delivery duct to a tip of a needle.

Thus the application device may be configured as a ready-to-use prefilled injection syringe.

According to this design the pinch seal can be effected in a very simple way by compressing the bung with the cap when resting on a peripheral portion of the holder so that the through channel extending through the bung is fully blocked. When the syringe shall be made ready for use, only the cap must be taken off, thereby transferring the syringe into the open state. Upon removal of the cap the pressure exerted by the cap on the bung is released so that the bung flexes outwardly under its own elastic force thereby freeing the through channel.

In addition, since the pinch seal is merely effected by compressing the elastic bung by the cap being supported on a peripheral portion of the holder, the operation of the syringe is not influenced by any clip tolerances, and activation of the syringe can be effected very reliably.

According to a further development of the invention the holder comprises at least one flexible arm that is pressed by the cap against the bung to generate a pinch seal of the through channel when being in the closed state.

This feature allows a very effective sealing of the through channel, since the flexible arm allows to generate a high pressure on the bung so as to effect a good pinch seal.

According to a further development of this design the at least one flexible arm is biased to the outside so as to release the pinch seal upon removal of the cap.

In this way an easy release of the pinch seal is effected upon removal of the cap. So the flexible arm allows to generate an effective pinch seal when being in the closed state and to reliably transition into the open state under its own biasing force.

Preferably the holder is made of a hard plastic material that generates a biasing force on the at least one flexible arm when pressed into the closed state.

In this way no additional biasing means, such as a spring means, is necessary to effect the desired biasing force.

The bung may preferably be made of a polypropylene, a thermo plastic elastomer (TPE), silicone rubber (LSR) or a different rubber type material.

Such a material provides the desired resilience to effect a good pinch seal in the compressed state and to release the pinch seal upon release of the outer pressure. Also this material can easily be molded into the desired shape.

According to a further development of the invention the tubular receptacle comprises a tubular extension being connected to the reminder of the tubular receptacle by a neck portion, wherein the holder comprises a hollow tubular portion that is mated to the tubular extension and comprises an inner rim portion protruding to the inside and engaging the neck portion for securing the holder on the tubular extension.

This allows for a simple and reliable design.

According to a further development of this design a collar is fitted onto the periphery of the hollow tubular portion for locking the inner rim portion onto the neck portion.

This allows for a simple assembly and a reliable securement of the holder on the tubular extension of the tubular receptacle.

According to a further development of the invention the bung comprises a peripheral flange being secured within the hollow tubular portion of the holder abutting the tubular extension of the receptacle.

Thereby reliable design and safe seal is facilitated.

The cap is preferably made from a rigid material, preferably from a hard plastic material.

This design allows an easy manufacture by molding and, in addition, provides sufficient rigidity to effect the necessary pressure for the pinch seal when being seated on the peripheral part of the holder.

According to a further development of the invention the cavity of the tubular receptacle is filled with a liquid which is sealed by a piston that is displaceable within the tubular receptacle by a piston rod.

In this way the single-use application device is filled with the desired liquid that can be expelled from the tip in the usual manner by exerting pressure on the piston rod for advancing the piston within the tubular receptacle.

According to a further embodiment of the invention the application device comprises a plurality of pinch seals coupled to different dispensable materials allowing a mixing of the materials after transfer of the pinch seals into the open state.

Thus a series of pinch seals may be used to seal of different dispensable materials and to effect a mixing of the materials when the pinch seals are transferred into the open state.

The object of the invention is further solved by a method of manufacturing an application device having a closed state at an end an open state, the method comprising the following steps:

provining a receptacle enclosing a cavity for receiving a liquid;

attaching a bung made of an elastic material to the receptacle so that a through channel extending through the bung is fluidly connected with the cavity;

providing a holder comprising a support for receiving a dispensing means fluidly connected with the through channel;

attaching the holder to the bung so that the bung is at least partially enclosed from the outside and that the dispensing means is fluidly connected with said through channel;

fitting a collar onto an end portion of the receptacle;

providing a removable cap;

attaching the cap onto a peripheral portion of the holder thereby pressing at least a portion of the holder onto the bung, thereby generating a pinch seal of the through channel; and securing an end portion of the cap within the collar.

Such a pre-manufactured application device may be filled with a drug material by a drug manufacturer by filling the cavity with the liquid, pasty or powdered material and sealing the filled cavity to the outside by inserting a piston held displaceably within the tubular cavity at an end of a piston rod. The application device is suitable for long-term storage of materials, such as drug materials.

The holder may support an injection needle or some kind of coupling such as a Luer-Lock thread or a bayonet-type connection.

Prior to filling the application device may be sterilized either in an assembled state or in a pre-assembled (open) state.

It is understood that the features of the invention mentioned above and those yet to be explained below can be used not only in the respective combinations indicated, but also in other combinations or in isolation, without leaving the scope of the present invention.

BRIEF DESCRIPTION OF THE DRAWINGS

Other features and advantages of the invention will become apparent from a preferred embodiment of the invention which will be described hereafter with reference to the drawings which are of merely exemplary nature without limiting the scope of the invention and in which:

FIG. 1 shows a perspective view of an application device according to the invention;

FIG. 2 shows an enlarged longitudinal partial section of the application device according to FIG. 1 in the region of the cap and the adjoining longitudinal end of the tubular receptacle, shown in the closed state with the cap attached; and FIG. 3 shows the application device of FIG. 2 in its open state, after removal of the cap.

DETAILED DESCRIPTION OF THE PREFERRED EMBODIMENT

In FIG. 1 a single-use application device according to the invention is shown in perspective view and depicted in total with reference numeral 10.

The application device 10 comprises a tubular receptacle 12 which is configured as a glass cylinder, having a first longitudinal end 13 and a second longitudinal end 14 and enclosing a cavity 15 that can be filled with a liquid. The cavity 15 is sealed to the outside by a piston 18 held at the end of a piston rod 20 and sealed against the interior wall of the cavity 15 by suitable sealing rings (not shown).

The application device 10 is shown in FIG. 1 in its closed state in which the cavity 15 is sealed against a needle supported on the first tubular end 13 of the tubular receptacle 12 and surrounded by a collar 24 and an attached cap 22.

For transferring the application device 10 from its closed state shown in FIG. 1 to an open state in which a liquid can be injected through the needle 32 shown in FIGS. 2 and 3, merely the cap 22 needs to be removed and thereafter the piston 22 can be advanced within the cavity 15 by pressing the end of the piston rod 20 with one finger while holding the tubular receptacle 12 at a gripping flange 16 provided on the second longitudinal end 14 with two fingers.

The details of the application device that allow a sealing of the cavity 15 against the needle 32 when being in its closed (or "dry") state and for transferring the application device into its open state in which liquid stored within the cavity 15 can be injected through a tip 38 of the needle 32 will be explained hereinafter with reference to FIGS. 2 and 3.

According to FIG. 2 the tubular receptacle 12 comprises a tubular extension 45 having a smaller diameter than the reminder of the tubular receptacle 12 and being connected to the remainder of the tubular receptacle 12 by a neck portion 44 defining a circumferential recess. Held within the inner wall of the tubular extension 45 is a bung 46 made of a polypropylene material or from TPE. The bung is of generally cylindrical shape resting with a peripheral flange 50 against the end surface of the tubular extension 45 and having a central through channel 48 that opens into the cavity 15 at one end and opens into a delivery duct 36 of the needle 32 at the other end.

In FIG. 3 the bung 46 is shown in its released state so that the central through channel 48 is not blocked by a pinch seal effected in the closed state shown in FIG. 2.

A holder 26 preferably made of a hard but elastic plastic material is attached onto the outer surface of the bung 46 and comprises an enlarged portion 40 having a larger outer diameter with a hollow tubular portion 41 that is fitted onto the peripheral flange 50 of the bung 46 and onto the tubular extension 45 of the tubular receptacle 12, thereby pressing the peripheral flange 50 of the bung 46 against the tubular extension of the receptacle 12. To effect a proper securement, the enlarged portion 40 comprises an inner rim portion 42 at its end remote from the needle 32 engaging the neck portion 44 of the tubular receptacle 12. To finally secure the holder 26 against removal from the tubular receptacle 12, in addition, a collar 24 is pressed onto the peripheral wall of the enlarged portion 40 using a press fit and rests against a rim portion protruding outwardly at the end of the enlarged portion 40.

The needle 32, usually made of stainless steel is fitted into a central opening 28 of the holder 26 and secured by an adhesive 30 or by another means so that the inner end of the needle 32 rests about flush with the through channel 48 of the bung 46.

The holder 26 at one side comprises a flexible arm 34 extending from a portion near the inner end of the needle 32 and having a free end remote from the needle 32. The flexible arm 34 has a cross section of a wedged shape having a larger thickness at its free end than at its other end that is connected to the remainder of the holder 26. The holder 26 is made from a hard but elastic plastic material that allows to bias the flexible arm 34 into the position shown in FIG. 3 so that the bung 46 is not compressed in the open state indicated by numeral 10' in FIG. 3.

For transferring the application device into a closed state in which the central through channel 48 of the bung 46 is sealed by the pinch seal 52 as shown in FIG. 2, the cap 22 needs to be attached on the holder 26. The cap 22 is inserted onto a peripheral portion of the holder 26 resting with its end within a slot provided between the peripheral portion of the holder 26 and the collar 54 and abutting against the enlarged portion 40 of the holder 26. In this closed state shown in FIG. 2 the flexible arm 34 is pressed by the cap 22 to the inside against the bung 46 thereby effecting the pinch seal 52 of the through channel 48, whereby the through channel 48 is effectively blocked.

This closed state shown in FIG. 2 is the ready-to-use state of the application device filled for instance with a medical drug by a drug manufacturer. The liquid containing the drug solution within cavity 15 is sealed against the needle 32 by the pinch seal 52. When the application device needs to be used, merely the cap 22 is pulled off from the holder 26 while holding the application device at the tubular receptacle 12. Once the cap 22 is removed, as shown in FIG. 3, the flexible arm 34 flexes to the outside under its own bias thereby releasing the central through channel 48 so that the drug solution contained in cavity 15 may then ejected out of the needle tip 38 by advancing the piston rod 20 thereby expelling the drug solution through the needle tip 38.

In case after a long storage period there should be some tendency of sticking between the two adjacent parts of the inner wall of the bung 46 effecting the pinch seal 52, the pressure generated by advancing the piston 18 into the cavity 15 will effectively remove any potential blockage of the pinch seal 52.

Alternatively, or in addition, the inner wall surface of the bung may comprise a coating (not shown) that is made from a material that prevents sticking and that prevents interaction with any drug material. Such a coating may, e.g. consist of parylene of PTFE (polytretrafluorethylene). This leads to a very reliable design.

What is claimed is:

1. An application device for applying a dispensable material, said application device having a closed state and an open state and comprising:
   a receptacle having a cavity for receiving a material;
   a collar fitted onto an end portion of said receptacle;
   an elastic part made of an elastic material and having a through channel engaging said cavity;
   a holder comprising a support for receiving a dispensing means fluidly connected with said through channel;
   a removable cap supported on a peripheral portion of said holder when the application device is in said closed state, said cap, when the application device is in the closed state, compressing said peripheral portion of said holder at least partially, thereby compressing said elastic part for effecting a pinch seal sealing said through channel; and
   a cap end portion provided on said cap, said cap end portion partially fitting into said collar, said collar thereby enclosing said cap end portion from outside so as to avoid leakage of said pinch seal;
   wherein said pinch seal is released when said cap is removed, thereby allowing delivery of material stored within said cavity through said through channel to said dispensing means;
   wherein said through channel of said elastic part further comprises an internal surface having a coating made of a material selected from the group consisting of parylene and PTFE, thereby preventing sticking of said internal surface and interaction with said material received within said cavity; and further
   wherein said collar is made of a plastic material more stable than the material from which said cap is made, thereby preventing a leakage of said pinch seal, even in case said cap should be prone to creeping during long-term storage.

2. An application device for applying a dispensable material, said application device having a closed state and an open state and comprising:
   a receptacle having a cavity for receiving a material;
   a collar fitted onto an end portion of said receptacle;
   an elastic part made of an elastic material and having a through channel engaging said cavity;
   a holder comprising a support for receiving a dispensing means fluidly connected with said through channel;
   a removable cap supported on a peripheral portion of said holder when the application device is in said closed state, said cap, when the application device is in the closed state, compressing said peripheral portion of said holder at least partially, thereby compressing said elastic part for effecting a pinch seal sealing said through channel; and
   a cap end portion provided on said cap, said cap end portion partially fitting into said collar, said collar thereby enclosing said cap end portion from outside so as to avoid leakage of said pinch seal;
   wherein said pinch seal is released when said cap is removed, thereby allowing delivery of material stored within said cavity through said through channel to said dispensing means;
   wherein said through channel of said elastic part further comprises an internal surface having a coating made of a material selected from the group consisting of parylene and PTFE, thereby preventing sticking of said internal surface and interaction with said material received within said cavity;
   wherein said receptacle is configured tubular comprising a tubular extension connected to a remainder of said receptacle by a neck portion, and wherein said holder comprises a hollow tubular portion that is mated to said tubular extension and comprises an inner rim portion protruding inwardly and engaging said neck portion for securing said holder on said tubular extension, and further
   wherein said collar is fitted onto a periphery of said hollow tubular portion for locking said inner rim portion onto said neck portion.

3. An application device for applying a dispensable material, said application device having a closed state and an open state and comprising:
   a receptacle having a cavity for receiving a material;
   a collar fitted onto an end portion of said receptacle;
   an elastic part made of an elastic material and having a through channel engaging said cavity;
   a holder comprising a support for receiving a dispensing means fluidly connected with said through channel;
   a removable cap supported on a peripheral portion of said holder when the application device is in said closed state, said cap, when the application device is in the closed state, compressing said peripheral portion of said holder at least partially, thereby compressing said elastic part for effecting a pinch seal sealing said through channel; and a cap end portion provided on said cap, said cap end portion partially fitting into said collar, said collar thereby enclosing said cap end portion from outside so as to avoid leakage of said pinch seal;

wherein said pinch seal is released when said cap is removed, thereby allowing delivery of material stored within said cavity through said through channel to said dispensing means; and further wherein said collar is made of a plastic material more stable than the material from which said cap is made, thereby preventing a leakage of said pinch seal, even in case said cap should be prone to creeping during long-term storage.

4. The application device of claim 3, wherein said elastic part further comprises a peripheral flange resting against a receptacle end portion of said receptacle, said peripheral flange being sealed against said receptacle end portion by said holder, said holder at least partially enclosing said peripheral flange and securing it to said receptacle end portion.

5. The application device of claim 3, wherein said dispensing means is configured as a part selected from the group consisting of a needle, a coupling, and a Luer-Lock thread.

6. The application device of claim 3, wherein said elastic part is configured as a bung at least partially received within said holder.

7. The application device of claim 6, wherein:
said receptacle is configured as a tubular receptacle enclosing said cavity for receiving a liquid;
said bung is held at a first longitudinal end of said tubular receptacle;
said dispensing means is configured as needle secured within said holder, said needle comprising a delivery duct fluidly connected with said through channel.

8. The application device of claim 3, wherein said holder comprises at least one flexible arm that is pressed against said elastic part to generate said pinch seal of said through channel when being in said closed state.

9. The application device of claim 8, wherein said at least one flexible arm is biased to the outside so as to release said pinch seal upon removal of said cap.

10. The application device of claim 8, wherein said holder is made of a hard plastic material that generates a biasing force on said at least one flexible arm when pressed into said closed state.

11. The application device of claim 3, wherein said holder is made of a material selected from the group consisting of a polypropylene, a thermo plastic elastomer (TPE), a rubber material, and a silicone rubber material (LSR).

12. The application device of claim 3, wherein said cavity of said receptacle is filled with a dispensable material which is sealed by a piston that is displaceable within said receptacle by a piston rod.

13. The application device of claim 3, further comprising a tamper evident means.

14. The application device of claim 3, further comprising a plurality of pinch seals coupled to different dispensable materials allowing a mixing of the materials after transfer of the pinch seals into said open state.

* * * * *